United States Patent
Weekamp et al.

(10) Patent No.: US 9,788,892 B2
(45) Date of Patent: Oct. 17, 2017

(54) CATHETER FOR OPEN-LOOP IRRIGATED ABLATION OF TISSUE

(75) Inventors: Johannes Wilhelmus Weekamp, Eindhoven (NL); Jan Frederik Suijver, Eindhoven (NL); Waltherus Cornelis Jozef Bierhoff, Eindhoven (NL); Szabolcs Deladi, Eindhoven (NL); Godefridus Antonius Harks, Eindhoven (NL)

(73) Assignee: Koninkljke Philips N.V., Eindhoven (NL)

( * ) Notice: Subject to any disclaimer, the term of this patent is extended or adjusted under 35 U.S.C. 154(b) by 1465 days.

(21) Appl. No.: 13/388,998

(22) PCT Filed: Aug. 26, 2010

(86) PCT No.: PCT/IB2010/053834
§ 371 (c)(1),
(2), (4) Date: Feb. 6, 2012

(87) PCT Pub. No.: WO2011/024133
PCT Pub. Date: Mar. 3, 2011

(65) Prior Publication Data
US 2012/0136351 A1    May 31, 2012

(30) Foreign Application Priority Data
Aug. 28, 2009  (EP) .................................. 09168911

(51) Int. Cl.
*A61B 8/14*  (2006.01)
*A61B 18/14*  (2006.01)
(Continued)

(52) U.S. Cl.
CPC .......... *A61B 18/1492* (2013.01); *A61B 8/445* (2013.01); *A61B 8/12* (2013.01);
(Continued)

(58) Field of Classification Search
CPC ............ A61B 8/461; A61B 8/467; A61B 8/44
USPC ........................................ 600/437, 462, 463
See application file for complete search history.

(56) References Cited

U.S. PATENT DOCUMENTS 6,216,027 B1 * 4/2001 Willis et al. .................. 600/424
6,950,689 B1   9/2005 Willis
(Continued)

FOREIGN PATENT DOCUMENTS

GB    2436066 A    9/2007
WO    9905971 A1   2/1999
(Continued)

*Primary Examiner* — Amanda Patton
*Assistant Examiner* — Philip C Edwards

(57) ABSTRACT

The present invention relates to a catheter (20) adapted for open-loop irrigated ablation, such as RF ablation, of a tissue (40). Said catheter has a distal tip (22) with an ablation entity (15) adapted for performing ablation of the tissue, an irrigation hole (21) and an ultrasound transducer (5) adapted for transmitting and/or receiving ultrasonic waves. The ultrasound transducer is disposed behind or in the irrigation hole of the catheter, so as to allow an irrigation fluid to flow out of the irrigation hole, and so as to allow transmitting and/or receiving the ultrasonic waves through the irrigation hole. The invention also relates to an imaging system and to a corresponding method for operating a catheter.

20 Claims, 4 Drawing Sheets

(51) Int. Cl.
*A61B 8/00* (2006.01)
*A61B 8/12* (2006.01)
*A61B 18/18* (2006.01)
*A61B 18/20* (2006.01)
*A61B 17/00* (2006.01)
*A61B 18/00* (2006.01)
*A61N 7/02* (2006.01)
*A61N 7/00* (2006.01)
*A61B 90/00* (2016.01)

(52) U.S. Cl.
CPC ........... *A61B 18/1815* (2013.01); *A61B 18/20* (2013.01); *A61B 2017/003* (2013.01); *A61B 2018/00029* (2013.01); *A61B 2018/00351* (2013.01); *A61B 2018/00357* (2013.01); *A61B 2018/1472* (2013.01); *A61B 2018/1497* (2013.01); *A61B 2090/3782* (2016.02); *A61B 2090/3784* (2016.02); *A61N 7/022* (2013.01); *A61N 2007/0078* (2013.01)

(56) References Cited

U.S. PATENT DOCUMENTS

2007/0167824 A1    7/2007  Lee
2010/0168570 A1*   7/2010  Sliwa et al. .................. 600/439

FOREIGN PATENT DOCUMENTS

WO    2004043272 A1    5/2004
WO    2009032421 A2   12/2009

* cited by examiner

CATHETER FOR OPEN-LOOP IRRIGATED ABLATION OF TISSUE

FIELD OF THE INVENTION

The present invention generally relates to a catheter adapted for open-loop irrigated ablation, such as RF ablation, of a tissue. The invention also relates to an imaging system, and to a corresponding method for operating a catheter.

BACKGROUND OF THE INVENTION

Ablation is a medical procedure where part of the heart, a tumor or, in general, any dysfunctional tissue is ablated so as to treat a medical disorder. In particular, such a procedure may be performed by means of catheters suitable for generating electromagnetic energy (in the range of optics, radio frequencies or microwaves) or ultrasonic energy.

In the minimally-invasive treatment of cardiac arrhythmias, for example, the radio frequency (RF) ablation catheter is the most commonly used therapy tool; in fact, it is referred to as the so-called "gold standard" in trials of novel ablation catheter designs. The last generation RF ablation catheters, so-called irrigation catheters, employ active cooling technologies, which consist in infusing an irrigation fluid through the catheter so as to cool the ablation electrode; this reduces the incidence of coagulum formation, produces a more controlled ablation and allows for a higher power delivery, the latter resulting in larger and deeper lesions.

In particular, there are two types of active cooling technologies: (i) closed-loop; and (ii) open-loop. In closed-loop irrigation, the irrigation fluid circulates within the catheter without being released into the blood. On the contrary, in open-loop irrigation, the irrigation fluid flows through the catheter and exits through tiny holes, called irrigation holes, usually placed around the tip of the catheter. Between the two technologies, the open-loop irrigated RF ablation is the one that reduces more the incidence of coagulum formation, as the irrigation fluid is directly in contact with the ablation electrode, the blood and the tissue surface. Yet, open-loop irrigated ablation procedures (electromagnetic—as well as ultrasound-based) still have significant drawbacks.

One major drawback relates to actively controlling the ablation settings during treatment. Currently, the therapist relies on his own expertise to determine the optimal parameters for ablation, e.g., power, temperature and duration. Note that these settings vary largely, due to sizable intra-patient differences of thickness of the local heart wall, perfusion, blood pressure and velocity, heart rhythm, etc. Although a highly-skilled therapist is able to succeed with this approach, it is not always the case, and there are serious consequences for the patient when an error occurs.

The two major therapy-related problems result from either the under-heating or the over-heating of the site. In the case of under-heating, the tissue is not sufficiently coagulated to form the arrhythmia-blocking lesion desired by the therapist. This can lead to persistent or recurring symptoms in the patient and the requirement for subsequent treatment(s), longer periods of hospitalization and greater risks of stroke and embolism. The other extreme, over-heating, either causes rupturing of the tissue at the treatment site, releasing potentially life-threatening particles into the blood stream, or causes damages to neighboring organs and tissues. In the case that other organs are affected, fistulas can develop and these are often life-threatening (e.g., a fistula in the esophagus has roughly a 75% mortality rate).

One of the options for monitoring the ablation process is the use of ultrasound technology, which can give information of the ablation effect on the tissue below the surface. WO 2009/032421 A2 discloses a catheter for ultrasound-guided ablation, where ablation electrodes are displaced on an outer catheter and ultrasound transducers are displaced in an inner catheter. Due to the relative displacement between electrodes and transducers, a number of ablation electrodes may interfere with the ultrasound propagation, thus degrading the overall image quality. In one embodiment, such an issue is avoided by reducing the thickness of the ablation electrodes. However, still a degraded signal-to-noise ratio and dynamical range is expected, due to the reflection and attenuation caused by the acoustical window. Specifically, these reverberations show up overlapping the relevant cardiac structures in the ultrasound data, thus requiring substantial post-processing.

Hence, there is the need for a solution that overcomes the aforementioned disadvantages and provides more adequate control of the ablation process; this would prevent injury and death from under-heating and over-heating in ablation procedures.

SUMMARY OF THE INVENTION

The present invention preferably seeks to alleviate or eliminate the above-mentioned disadvantage of degraded monitoring performance when using ultrasound technology in an ablation catheter. In particular, it may be seen as an object of the present invention to provide an ablation catheter which would offer a more adequate control of the ablation process by means of feedback of the lesion development in the tissue and information about the depth of the lesion with respect to the thickness of the tissue at the treatment site.

This object and several other objects are obtained in a first aspect of the present invention by a catheter adapted for open-loop irrigated ablation of a tissue, where such an ablation may be carried out by means of electromagnetic energy (in the range of optics, radio frequencies or microwaves) or ultrasonic energy.

In particular, the present invention relates to a catheter adapted for open-loop irrigated ablation of a tissue, said catheter comprising a distal tip, wherein the distal tip comprises:

an ablation entity adapted for performing ablation of the tissue;

an irrigation hole; and an ultrasound transducer adapted for transmitting and/or receiving ultrasonic waves;

wherein the ultrasound transducer is disposed behind or in the irrigation hole of the catheter, so as to allow an irrigation fluid to flow out of the irrigation hole, and so as to allow transmitting and/or receiving the ultrasonic waves through the irrigation hole.

It may be seen as an advantage that by placing the ultrasound transducer behind or in the irrigation hole there is no need for an acoustically transparent window. The benefit is a better signal-to-noise ratio and an increased dynamical range due to the elimination of reflection and attenuation caused by the acoustical window. Specifically, the second-order and higher-order reflections from the acoustic window (so-called ultrasonic reverberations) are completely avoided. This is a major improvement that permits to avoid substantial post-processing due to the fact that these reverberations usually show up overlapping the relevant cardiac structures in the ultrasound data.

In the context of the present application, the term "in" refers to the displacement of the ultrasound transducer within the irrigation hole itself, whereas the term "behind" refers to any position inside the distal tip which is not within the irrigation hole and which permits to the ultrasonic waves generated from the ultrasound transducer to flow through the irrigation hole undisturbed or with minimal interference from the distal tip. In particular, this may also imply that the ultrasound transducer may be able to direct its ultrasonic waves towards the irrigation hole from any displacement.

In the context of the present application, the term "ablation entity" refers to a laser in case of optical-based ablation, an electrode in case of RF- and microwave-based ablation and to a transducer in case of ultrasound-based ablation.

The ultrasound transducer in the catheter is preferably applied for monitoring or imaging the local cardiac tissue, the ablation process in said cardiac tissue or parameters related, directly or indirectly, to the ablation process. In the context of the present invention, monitoring is to be construed broadly. It includes both 1D monitoring, i.e. detecting reflected intensities along the line of sight as well as 2D imaging where an array of transducers are applied to generate a 2D image as well as time resolved imaging (so-called ultrasound M-mode imaging). In principle also 3D imaging may be obtained. In catheter-based monitoring, it is presently normal to use (time resolved) 1D or 2D monitoring due to space constraints in the distal end region, i.e. in the tip region.

In a useful embodiment, the catheter is adapted for open-loop irrigated radio frequency (RF) ablation.

In a beneficial embodiment, the distal tip comprises a plurality of irrigation holes.

In a valuable embodiment, the distal tip comprises a plurality of ultrasound transducers.

In an advantageous embodiment, at least a sub-set of the plurality of ultrasound transducers is individually addressable; therefore, a multi-plot screen is envisaged for the signal presentation.

In yet a useful embodiment, the number of ultrasound transducers is equal to or less than the number of irrigation holes.

In yet a beneficial embodiment with a plurality of transducers and a plurality of irrigation holes, each ultrasound transducer is disposed behind or in one corresponding irrigation hole. Thus, there may be a one-to-one relation between a transducer and a corresponding hole. This allows avoiding the inclusion of acoustically transparent windows, which inevitably cause some propagation losses, and results, e.g., in images of higher quality when monitoring an ablation process.

In yet a valuable embodiment, the diameter of the irrigation hole is larger than the diameter of the ultrasound transducer. This lowers ultrasonic reverberations and thereby improves the signal-to-noise (S/N) of the monitoring or imaging process during positioning and/or during the ablation process.

In yet an advantageous embodiment, the plurality of ultrasound transducers is provided with a common ultrasound backing material. As a consequence, it is not needed anymore to have individual backing for each transducer. Very significant space can be spared in the catheter by this technique, and furthermore enables signal reception from various directions. The envisaged embodiment should enable ablation and lesion monitoring by a catheter in the range of positions from perpendicular to parallel with respect to the tissue.

In another useful embodiment, the irrigation holes are arranged so as to compose a substantially symmetric configuration.

In another beneficial embodiment, the ablation entity defines an area on the distal tip embracing one or more irrigation holes.

In another valuable embodiment, the distal tip comprises a plurality of ablation entities. In another advantageous embodiment, at least a sub-set of the plurality of ablation entities is individually addressable.

In yet another useful embodiment, the ablation entity is a ring of electrically conductive material encircling the irrigation hole in a concentric manner.

In yet another beneficial embodiment, the number of ablation entities is equal to or less than the number of irrigation holes, each ablation entity being a ring of electrically conductive material encircling one irrigation hole in a concentric manner.

It is seen as an advantage of the above embodiments that the electromagnetic or acoustic energy generated by the one or more ablation entities can be better controlled during the ablation process.

In yet another valuable embodiment, one or more ultrasound transducers are displaceable within the catheter.

In a second aspect, the present invention relates to a system for performing ablation, the system comprising a controllable energy source; a sample arm coupled to the energy source, the sample arm having at its distal end a catheter according to the first aspect; and an imaging or monitoring device coupled to the energy source and the sample arm.

In a third aspect, the present invention relates to a method for performing ablation comprising the steps of:

providing a catheter adapted for open-loop irrigated ablation of a tissue, said catheter comprising a distal tip;

performing ablation of the tissue with an ablation entity comprised in the distal tip;

providing an irrigation hole; and transmitting and/or receiving ultrasonic waves with an ultrasound transducer;

wherein the ultrasound transducer is disposed behind or in the irrigation hole of the catheter, so as to allow an irrigation fluid to flow out of the irrigation hole, and so as to allow transmitting and/or receiving the ultrasonic waves through the irrigation hole.

The first, second and third aspects of the present invention may each be combined with any of the other aspects. These and other aspects of the present invention will be apparent from and elucidated with reference to the embodiments described hereinafter.

BRIEF DESCRIPTION OF THE DRAWINGS

Embodiments of the present invention will be described, by way of example only, with reference to the drawings, in which.

DESCRIPTION OF EMBODIMENTS

Embodiments of the present invention are disclosed in the following.

Figure 1:
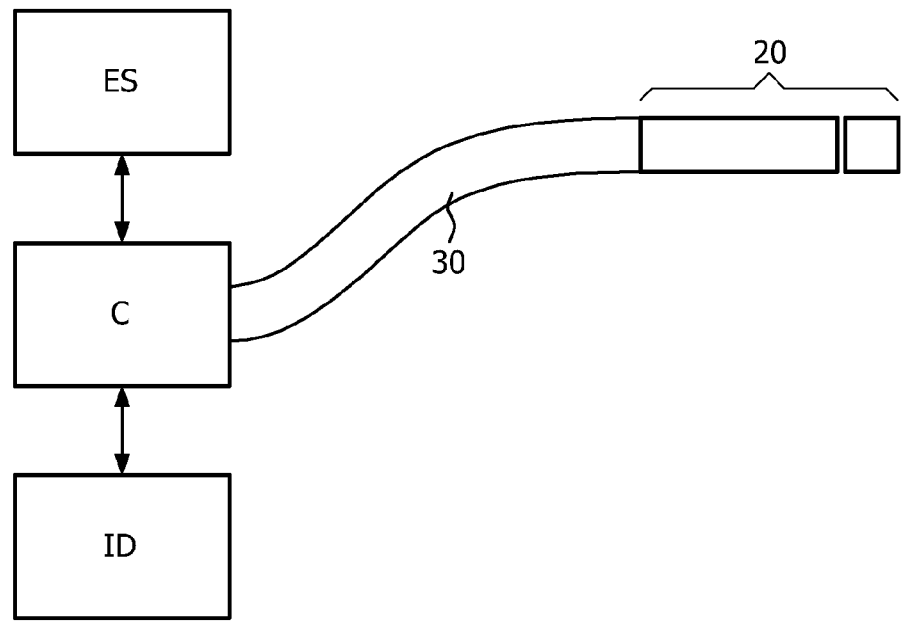
FIG. 1 shows an imaging system for performing ablation according to the present invention.

FIG. 1 shows a general system for performing ablation, the system comprising a controllable energy source (ES) for providing energy to the source of ablation and/or the ultrasonic transducer (neither shown in this figure). Additionally, a sample arm 30 is coupled to the energy source, the sample arm having at its distal end a catheter 20 according to the present invention. An imaging or monitoring device (ID) is coupled (C) to the energy source (ES) and the sample arm 30.

As used herein, the term "ablation" refers to any kind of suitable ablation within the teaching and general principle of the present invention. Thus, it could be RF-(incl. microwave), laser- and ultrasound-based ablation. The invention can be used in tissue imaging during treatment, for example treatment of heart arrhythmias or in oncology. The aim of the treatment is to follow the progression of lesion formation during the procedure and to help for decision support (stop-go).

Figure 2:
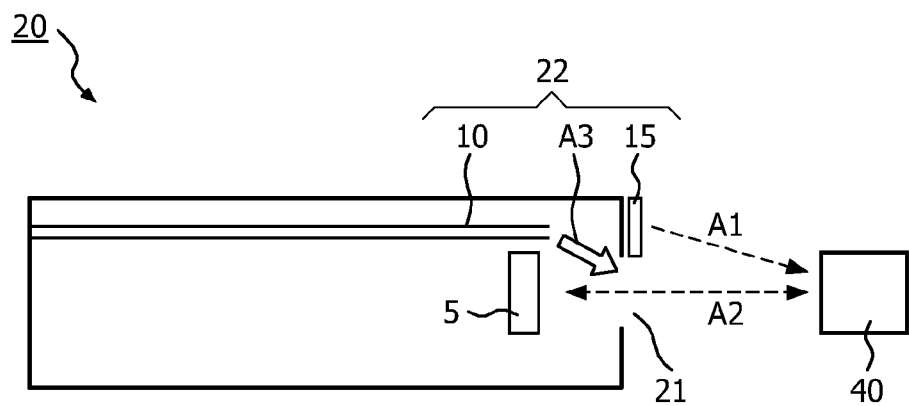
FIG. 2 shows a schematic, cross-sectional drawing of a catheter adapted for open-loop irrigated ablation of a tissue according to the present invention.

FIG. 2 shows a schematic, cross-sectional drawing of a catheter 20 adapted for open-loop irrigated ablation of a tissue 40. The catheter 20 is adapted for open-loop irrigated ablation, e.g. RF ablation, of a tissue 40, the catheter 20 having a distal tip 22, i.e. the right-hand part of the shown catheter embraced by the bracket, where the distal tip comprises an ablation entity 15 adapted for performing ablation of the tissue 40. Note that although in FIG. 2 the ablation entity is depicted as covering only the forward side of the catheter, it may also cover the catheter's sideward. The radiation for performing ablation is schematically shown by dotted arrow A1. The required wiring for energizing and/or controlling the ablation entity is not shown in this figure for clarity. In addition, an irrigation hole 21 is provided. The irrigation fluid is flowing out of a dedicated irrigation fluid conduct 10, e.g. a flexible tube, as indicated schematically by solid arrow A3. The irrigation fluid is functioning as an acoustic coupling medium, which may be defined as a medium substantially transparent to ultrasonic waves, such as a saline solution or water or other similar liquids available to the skilled person implementing the invention.

Further, an ultrasound transducer 5 is positioned in the distal tip, the transducer being adapted for transmitting and/or receiving ultrasonic waves as schematically indicated by double-headed dotted arrow A2 in FIG. 2. In the most general form of the invention, the ultrasound transducer is disposed behind (as in this figure) or in the irrigation hole 21 of the catheter 20, so as to allow an irrigation fluid A3 to flow out of the irrigation hole, and so as to allow transmitting and/or receiving the ultrasonic waves through the same irrigation hole 21.

Advantageously, the catheter 20 may be used for open-loop irrigated radio frequency (RF) ablation.

Figure 3:
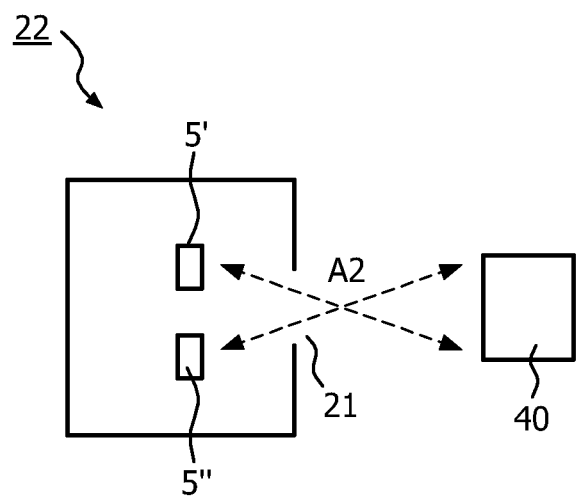
FIGS. 3 and 4 show schematic, cross-sectional drawings of other embodiments of a catheter according to the present invention.

FIG. 3 shows a schematic, cross-sectional drawing of a catheter 20 similar to FIG. 2, but with the difference that the distal tip 22 comprises a plurality of ultrasound transducers, i.e. transducer 5' and 5". Some parts are left out for clarity, e.g. the ablation entity. In this embodiment, two transducers are placed behind but shifted to the sides of the hole 21 and directing ultrasonic waves obliquely into the hole 21.

It is contemplated that the ultrasound transducers 5' and 5" could be used for monitoring the tissue itself.

It is also contemplated that some transducers could be only emitting whereas other transducers could be only receiving, e.g. transducer 5' could be transmitting and transducer 5" could be receiving.

Figure 4:
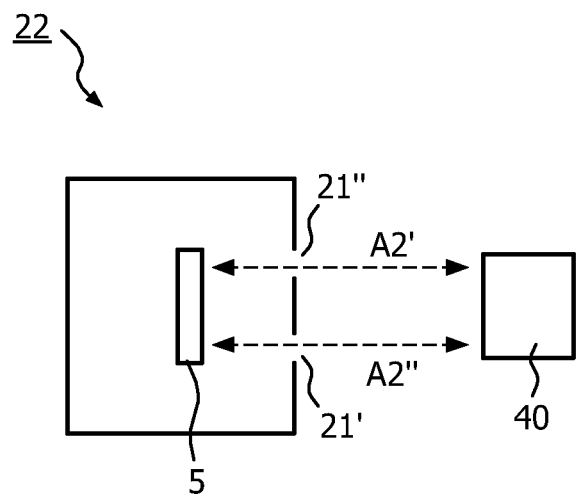

FIG. 4 shows a schematic, cross-sectional drawing of a catheter 20 similar to FIGS. 2 and 3, but with the difference that the distal tip comprises a plurality of irrigation holes, i.e. holes 21' and 21". In this embodiment, two holes are placed at the distal end of the catheter 20. The transducer 5 emits and/or receives ultrasonic waves as schematically indicated by double-headed dotted arrows A2' and A2". The width of the material (typically metal) between the holes 21' and 21" may be substantially smaller than the width of the transducer, e.g. 10%, 5% or less, of the transducer width. For simplicity transducer 5 is shown as a single transducer; however, it may also be an array of transducers.

Figure 5:
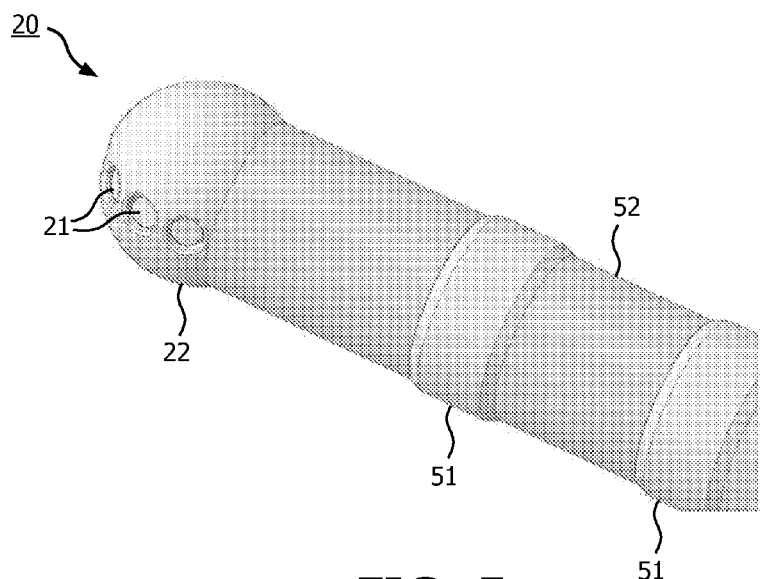
FIG. 5 shows a perspective view of a catheter according to the present invention.

FIG. 5 shows a perspective view of a catheter 20 according to the present invention. The tip 22 of the catheter is mounted on a flexible tube 52 for easy manipulation through the human body. Additional ring shaped electrodes 51 on the tube can measure properties like resistance and temperature. The tube 52 will contain the needed wires for addressing the transducers and will supply the irrigation liquid.

Figure 6:
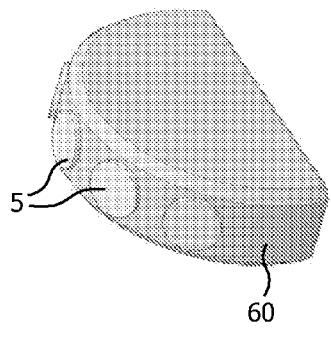
FIGS. 6 and 7 show parts of a catheter according to the present invention
Figure 7:
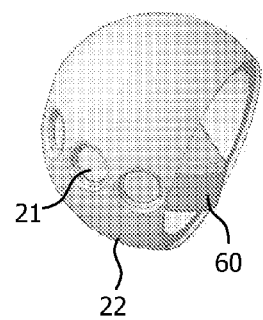

FIGS. 6 and 7 show parts of a catheter according to the present invention.

FIG. 6 shows a preferred embodiment of the invention, where the array of small transducers 5 is used with one common backing block 60. The transducers remain individually addressable. The one or more ultrasound transducers are typically piezoelectric transducers, but other transducers may be applied. FIG. 6 shows a backing block with 5 individually addressable transducers. For simplicity, the wiring is not shown. The transducers are individually addressable; therefore a multi-plot screen is envisaged for the signal presentation. Alternatively, the desired piece of the transducer can be selected for ablation decision support, depending on the orientation of the catheter with respect to the tissue during ablation.

Typical diameter of such transducers 5 can be as small as 0.5 mm. Individual single element transducers of this size can monitor tissue contrast (as is demonstrated for example in the IVUS catheters sold by the USA companies Volcano and Boston Scientific). By placing multiple piezo-electrical discs 5 on a common backing material, it is not needed anymore to have individual backing for transducers. Very significant space can be spared in the catheter 20 by this technique, and furthermore enables signal reception from various directions. The envisaged embodiment should enable ablation and lesion monitoring by a catheter in the range of positions from perpendicular to parallel with respect to the tissue.

FIG. 7 shows the common backing block 60 inserted within the distal tip 22, the block 60 being mounted within the tip 22 so that each ultrasound transducer is disposed behind one corresponding irrigation hole 21. Furthermore, the diameter of the irrigation hole 21 is preferably larger than the diameter of the ultrasound transducer to lower ultrasonic reverberations and thereby improve the signal-to-noise (S/N) of the monitoring or imaging process during positioning and/or during the ablation process. In this embodiment, the ablation entity has a hemispherical shape covering the tip 21, but with holes in the ablation entity for the irrigation holes 21.

The irrigation nozzles (i.e. conduit 10 in FIG. 2) should be tailored according to the acoustical beam size produced by the piezo-elements 5; therefore, they should be larger than the diameter of the beam in order to avoid diffraction from the edge of the nozzles, which disturbs the ultrasound contrast coming from the tissue. For example an irrigation hole diameter of 1.5 times the acoustical beam, and an ultrasound beam with no more than 5 degrees divergence would be preferred.

FIG. 7 shows the ablation tip with the transducers inside. The ablation occurs with the metallic part of the tip 22, or alternatively the tip might be of a certain polymer/plastic and subsequently coated with electrically conductive material. The formation of lesion in front of the transducer elements does not suffer in critical way due to lack of ablation entity right in front of them.

It has been more specifically been demonstrated that it is feasible to use ring-shaped electrodes, cf. FIGS. 8D and 8E below. In this case, the depth of the lesion will have a slightly different profile, however this is strictly linked to the specific form of the ablation entity, and it is highly predictable. Experiments were carried out by using ring-shaped electrodes, and the ablation outcome was outstanding.

Figure 8:
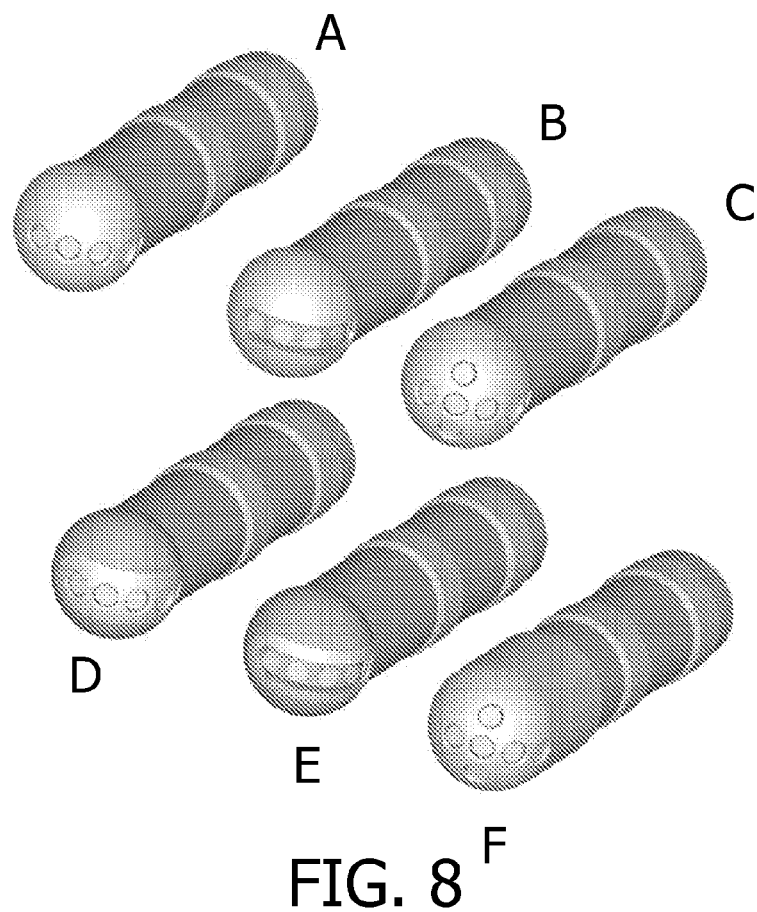
FIG. 8 shows perspective views of various configurations for a catheter tip according to the present invention.

FIG. 8 shows perspective views of various configurations for a catheter tip according to the present invention.

FIG. 8A is a configuration where the ablation entity covers most of the tip but with dedicated holes for each irrigation hole.

FIG. 8B is a configuration where the ablation entity covers most of the tip but with one elongated hole for the assembly of irrigation holes.

FIG. 8C is a configuration similar to FIG. 8A where the ablation entity covers most of the tip but with dedicated holes for each irrigation hole both in a horizontal and a perpendicular longitudinal direction as shown in the figure.

FIG. 8D is a configuration where the ablation entity covers a limited area of the tip forming a ring-shaped electrode with one hole for each irrigation hole.

FIG. 8E is a configuration where the ablation entity covers a limited area of the tip forming a ring-shaped electrode with one elongated hole for the plurality of irrigation holes.

FIG. 8F is a configuration similar to the configuration shown in FIG. 8A where the ablation entity covers most of the tip with dedicated holes for each irrigation hole and where the tip is extending along a larger part of the tip (as compared to FIG. 8A).

Advantageously, the irrigation holes in the catheter may be arranged so as to compose a substantially symmetric configuration. The symmetry may be a rotational symmetry around a central axis of the catheter, or mirror symmetry around a central axis of the catheter.

Figure 9:
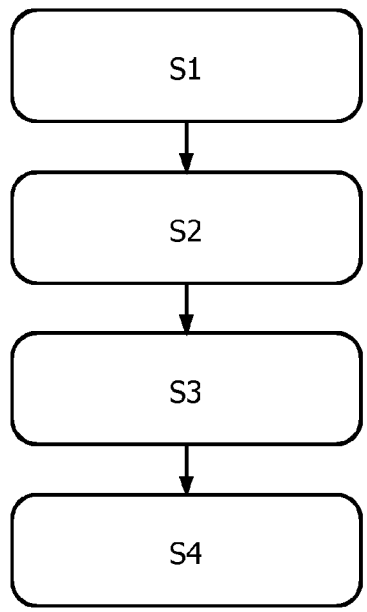
FIG. 9 is a flow chart of a method according to the present invention.

FIG. 9 is a flow chart of a method for performing ablation according to the present invention. Such a method comprises the steps of:

providing S1 a catheter adapted for open-loop irrigated ablation of a tissue, said catheter comprising a distal tip;
performing S2 ablation of the tissue with an ablation entity comprised in the distal tip;
providing S3 an irrigation hole; and
transmitting and/or receiving S4 ultrasonic waves with an ultrasound transducer;
wherein the ultrasound transducer is disposed behind or in the irrigation hole of the catheter, so as to allow an irrigation fluid to flow out of the irrigation hole, and so as to allow transmitting and/or receiving the ultrasonic waves through the irrigation hole.

The invention can be implemented in any suitable form including hardware, software, firmware or any combination of these. The invention or some features of the invention can be implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second", etc. do not preclude a plurality. Furthermore, reference signs in the claims shall not be construed as limiting the scope.

The invention claimed is:

1. A catheter adapted for open-loop irrigated ablation of a tissue, said catheter comprising a distal tip, wherein the distal tip includes:
   an ablation entity adapted for performing ablation of the tissue;
   an irrigation hole; and
   an ultrasound transducer adapted for transmitting and/or receiving ultrasonic waves;
      wherein the ultrasound transducer is disposed behind or in the irrigation hole of the catheter, so as to allow an irrigation fluid to flow out of the irrigation hole, and so as to allow transmitting and/or receiving the ultrasonic waves through the irrigation hole.

2. A catheter according to claim 1, wherein the distal tip includes a plurality of irrigation holes.

3. A catheter according to claim 2, wherein the distal tip includes a plurality of ultrasound transducers; and
   wherein each ultrasound transducer is disposed behind or in one corresponding irrigation hole.

4. A catheter according to claim 2, wherein the ablation entity defines an area on the distal tip embracing one or more irrigation holes.

5. A catheter according to claim 1, wherein the distal tip includes a plurality of ultrasound transducers.

6. A catheter according to claim 5, wherein at least a sub-set of the plurality of ultrasound transducers is individually addressable.

7. A catheter according to claim 5,
   wherein the distal tip includes a plurality of irrigation holes; and
   wherein a number of ultrasound transducers is equal to or less than a number of irrigation holes.

8. A catheter according to claim 5, wherein the plurality of ultrasound transducers is provided with a common ultrasound backing material.

9. A catheter according to claim 1, wherein a diameter of the irrigation hole is larger than a diameter of the ultrasound transducer.

10. A catheter according to claim 1, wherein the distal tip includes a plurality of ablation entities.

11. A catheter according to claim 10, wherein a number of ablation entities is equal to or less than a number of irrigation holes.

12. A catheter according to claim 11, wherein each ablation entity is a ring of electrically conductive material encircling one irrigation hole in a concentric manner.

13. A catheter according to claim 1, wherein the ablation entity is a ring of electrically conductive material encircling the irrigation hole in a concentric manner.

14. A catheter according to claim 13, wherein at least a sub-set of the plurality of ablation entities is individually addressable.

15. A catheter according to claim 1, wherein the ultrasound transducers is displaceable within the catheter.

16. A catheter according to claim 1, wherein the ultrasound transducer is disposed behind or in the irrigation hole of the catheter so as to permit the ultrasonic waves generated from the ultrasound transducer to flow through the irrigation hole undisturbed or with minimal interference from the distal tip.

17. A system for performing ablation, the system comprising:
 a controllable energy source,
 a sample arm coupled to the energy source, the sample arm having at its distal end a catheter according to claim 1; and
 an imaging or monitoring device coupled to the energy source and the sample arm.

18. A system according to claim 17, wherein the ultrasound transducer is disposed behind or in the irrigation hole of the catheter so as to permit the ultrasonic waves generated from the ultrasound transducer to flow through the irrigation role undisturbed or with minimal interference from the distal tip.

19. A method for performing ablation, the method comprising:
 providing a catheter adapted for open-loop irrigated ablation of a tissue, said catheter including a distal tip;
 performing ablation of the tissue with an ablation entity included in the distal tip;
 providing an irrigation hole included in the distal tip; and
 transmitting and/or receiving ultrasonic waves with an ultrasound transducer included in the distal tip;
  wherein the ultrasound transducer is disposed behind or in the irrigation hole of the catheter, so as to allow an irrigation fluid to flow out of the irrigation hole, and so as to allow transmitting and/or receiving the ultrasonic waves through the irrigation hole.

20. A method according to claim 19, wherein the ultrasound transducer is disposed behind or in the irrigation hole of the catheter so as to permit the ultrasonic waves generated from the ultrasound-transducer to flow-through the irrigation hole undisturbed or with minimal interference from the distal tip.

* * * * *